United States Patent [19]

Pagani et al.

[11] Patent Number: 5,380,943
[45] Date of Patent: * Jan. 10, 1995

[54] PROCESS AND PLANT FOR THE PRODUCTION OF UREA WITH DIFFERENTIATED YIELD REACTION SPACES

[75] Inventors: Giorgio Pagani, Lugano; Umberto Zardi, Breganzona, both of Switzerland

[73] Assignee: Urea Casale S.A., Lugano, Switzerland

[*] Notice: The portion of the term of this patent subsequent to Jan. 4, 2011 has been disclaimed.

[21] Appl. No.: 947,287

[22] Filed: Sep. 16, 1992

[30] Foreign Application Priority Data

Nov. 14, 1991 [CH] Switzerland ............. 03325/91-2

[51] Int. Cl.⁶ .................................. C07C 273/04
[52] U.S. Cl. .................................. 564/67; 564/63; 564/69; 564/70; 564/71
[58] Field of Search .............. 564/67, 63, 69, 70, 564/71, 72

[56] References Cited

U.S. PATENT DOCUMENTS

| | | | |
|---|---|---|---|
| 4,504,679 | 3/1985 | Inoue et al. | 564/67 |
| 4,670,588 | 6/1987 | Zardi | 564/72 |
| 4,801,745 | 1/1989 | Meessen et al. | 564/70 |
| 5,276,183 | 1/1994 | Pagani et al. | 564/67 |

FOREIGN PATENT DOCUMENTS

| | | |
|---|---|---|
| 0497215 | 8/1992 | European Pat. Off. |
| 1643092 | 3/1971 | Germany |
| 1124547 | 8/1968 | United Kingdom |

*Primary Examiner*—Richard L. Raymond
*Assistant Examiner*—Shailendra Kumar
*Attorney, Agent, or Firm*—Ostrolenk, Faber, Gerb & Soffen

[57] ABSTRACT

Process for the industrial synthesis of urea, by reacting ammonia ($NH_3$) and carbon dioxide ($CO_2$) in at least one reaction space, at high pressures and temperatures and by recirculating at least part of the non-reacted products obtained in a recovery section, characterized by the fact that the following takes place : a synthesis reaction A) between highly pure reagents, and a synthesis reaction B) between less pure reagents, substantially recycled from the said recovery section, the reaction A) being either of adiabatic type A1) or with partial reaction heat removal A2).

12 Claims, 4 Drawing Sheets

PROCESS AND PLANT FOR THE PRODUCTION OF UREA WITH DIFFERENTIATED YIELD REACTION SPACES

BACKGROUND OF THE INVENTION

1. Field of the Invention

This invention concerns a process for the industrial production of urea by reacting ammonia ($NH_3$) and carbon dioxide ($CO_2$) in a synthesis section consisting of many differentiated yield reaction spaces, in one of these spaces a majority part of the total conversion occurs by feeding it with highly pure reagents, and in the other of these spaces the remaining minority part of the conversion occurs by feeding it with less pure reagents that have been substantially recirculated by a recovery section.

This invention comprises also the plants for the installation of said process.

2. Description of the Related Art

A method for the synthesis of urea of the type set forth in the introduction is described in the Swiss patent application No. 03216/90-1 deposited on Oct. 3rd, 1990, by the Applicant.

The plant (a "once through type") for the carrying out of this process comprises: a first high-yield reactor fed with $CO_2$ and fresh $NH_3$ from the outside and with very pure recovery $NH_3$; a second reactor, parallel with the first, with a less high yield than the first and substantially fed with reagents from the recovery mixture; and a system or recovery section for the recovery of reaction mixtures obtained from said first and second reactors.

In another Swiss patent application, No. 00264/91-4, filed Jan. 29, 1991, the Applicant has described an embodiment of the process according to said first patent application, which lends to a particularly efficient and advantageous result, because of the small investment and minimum consumption of energy it requires, characteristically the majority synthesis reaction stage (A) with high-yield, between highly pure reagents, operating at a higher pressure (Pmax), for instance, above 300 abs and preferably around 400 bar abs, is followed by a flash stage F1 operating at pressures lower than approximately 200 bar abs, the gaseous effluent GF1 of the above mentioned flash stage F1 being fed to a minority synthesis reaction stage B with less pure reagents operating at a pressure lower than 200 bar abs, while the liquid effluent EL1 of the above mentioned flash stage, together with the effluent EB from minority reaction stage B operating in parallel to the majority reaction stage A, are fed to a recovery section RE consisting of two decomposition stages D1 and D2 operating in series: the first D1 being lower than 100 bar abs preferably at 50 bar abs; the second D2 working at a pressure lower than 50 bar abs preferably at 20 bar abs. Each decomposition stage consists of a decomposer D1 and D2 respectively (heat exchangers for the distillation of reagents not transformed into urea), whose gas effluents, consisting of $NH_3 + CO_2 + H_2O$, feed a condensation system with direct heat recovery from the process, where the partial condensation of said effluents is carried out and then completed in a fractionating column with a head condenser.

SUMMARY OF THE INVENTION

In the uninterrupted research and experimentation in this important technical field, the Applicant had succeeded, not without surprise, to perfect articulated and flexible processes that will cope, with particularly efficient and advantageous embodiments, with the most varied and frequent requirements by minimizing each time the investment costs and/or energy consumptions, and by maximizing the yields by adopting the most appropriate operating conditions according to the capacity of the plant.

These objectives are reached with the process according to the invention that is characterized by the fact that the synthesis is maximized A) by carrying out the reaction in two possible and distinctive ways, i.e.: A1 in adiabatic conditions, at pressures higher than 300 bar, at temperatures above 200° C. and at a $NH_3/CO_2$ molar ratio higher than 4, and A2) by removing heat from the reaction carried out at a pressure lower than 300 bar, at a temperature not higher than 200° C. and with a $NH_3/CO_2$ molar ratio not higher than 4. Further characteristics of the invention are deducible from the claims hereunder.

BRIEF DESCRIPTION OF THE DRAWING

The various aspects and advantages of the invention will be better illustrated by the following description of one of the possible embodiments with heat removal, (preferred, but not limitative), shown in the attached drawings, in which FIGS. 1 and 2, although not respectively, are process flow diagrams.

DETAILED DESCRIPTION OF THE PREFERRED EMBODIMENTS

Differentiated Yield Process HEC

This new process has the advantage of requiring low energy and inexpensive recycle units.

Moreover, the type of reactor for the reaction A) (a "once-through" type) has a high efficiency, great reliability, is substantially corrosion free, and requires low residence time i.e. small dimensions.

The process consists of the following sections:

a) synthesis section with two reactors (R1, R2) in parallel;

b) a medium pressure recycling section with one decomposition stage surmounted by an ammonia fractionating system to produce a purified urea solution, a carbamate solution and pure ammonia streams that are sent respectively to the secondary converter (R2) (carbamate solution), and to the main converter ($NH_3$);

c) concentration section of the solution and for finishing.

EXAMPLE 1

Figure 1:
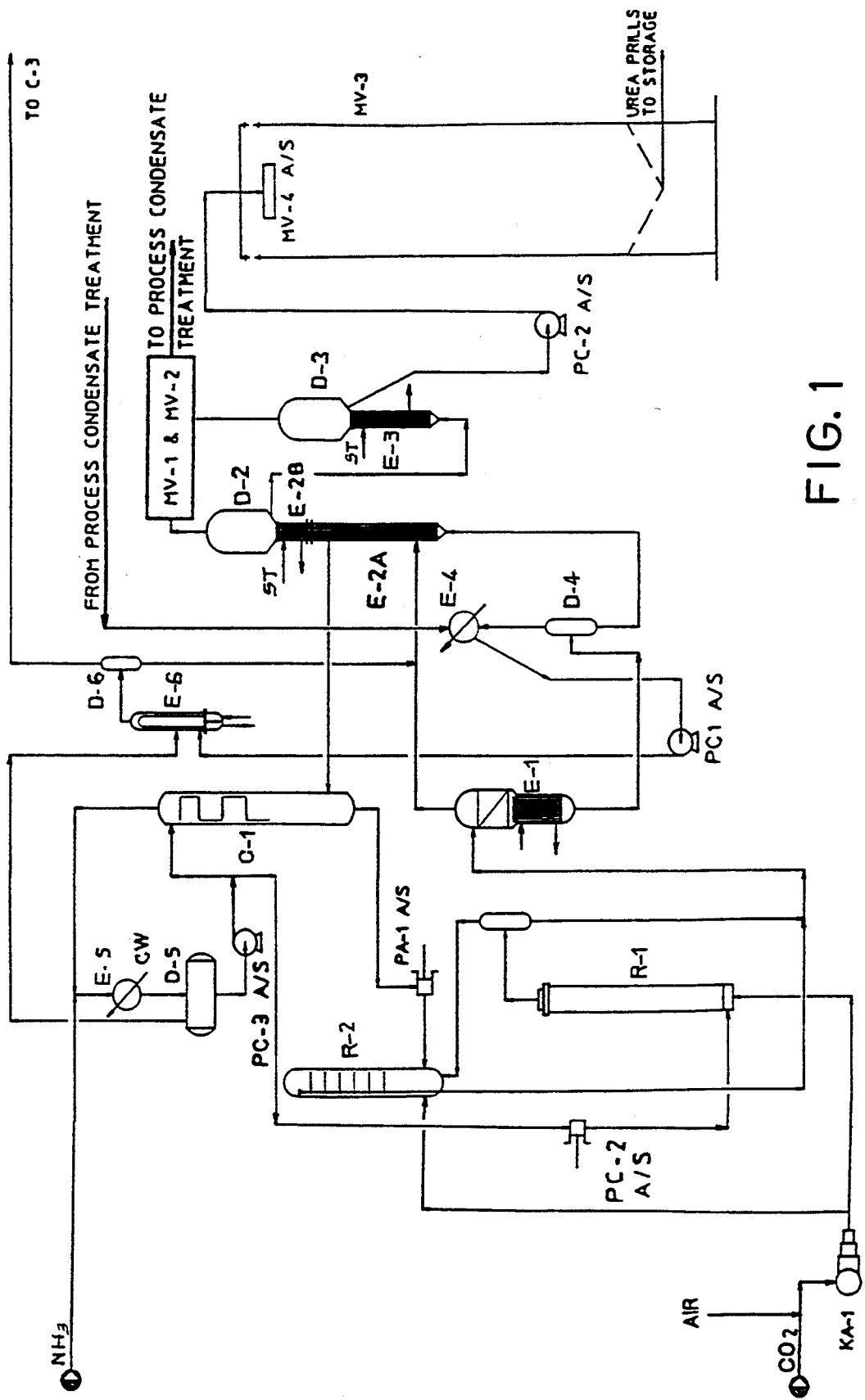

Adiabatic Process (FIG. 1)

The main characteristic of the process is that the heat developed by the reaction

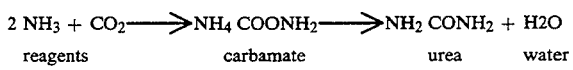

is utilized to bring the reagents to the reaction temperature. The operating conditions of the majority reaction preferably are: temperature reaction ≥200° C.; pressure >300 bar; NH3/CO2>4; yield >75%.

The majority reaction A1 is carried out in the following conditions:

| | |
|---|---|
| NH3/CO2 mol | 4.5 |
| H20/CO2 mol | 0 |
| CO2 conversion | 80% |
| NH3 inlet temperature | ≈ 40° C. |
| CO2 inlet temperature | ≈ 150° C. |
| Reaction temperature | 215° C. |
| Pressure | 400 bar abs |
| Conversion yield CO2 | 80% |
| Reactor lining | zirconium |

Characteristically the majority part of the reaction heat used to heat the $NH_3$ in excess from 40° C. to 215° C. In particular 90% of the $CO_2$ feeds R1, while 10% goes to the reactor R2.

The urea solution from reactor R1 is subjected to flash from 400 to 150 bar in the separator D1.

The vapours produced from the flash in D1 (substantially ammonia) are sent to R2, whereas the urea solution in D1 is mixed with the solution from reactor R2 and feeds the MP decomposer.

The operating conditions of the secondary reactor are:

| | |
|---|---|
| NH3/CO2 molar | 4.5 |
| H20/CO2 molar | 1.2 |
| Conversion yield | 61% |
| Pressure | 150 bar ass. |
| Temperature | 190° C. |

72% of the urea production is obtained in R1, while the remaining 28% is obtained in R2.

The weighed average efficiency of the two reactors is close to 75%, which is very high in comparison to the efficiency of very recent processes.

The urea solution is distilled in said decomposer E1 operating at 18 bar that can be falling-film type of upflow type. The solution obtained in E1 is carried for flash at 3.5 bar releasing vapours rich in $NH_3$. The urea solution then passes in to the vacuum section where it is concentrated up to 96% w in the first evaporator E2 that operates at 0.35 bar, and then up to 99.7% w in the second evaporator E3 operating at 0.05 bar.

The vapours obtained in this way in E1 are partially condensed in the first part of the first evaporator E2-A, in which a part of the process heat is recovered (with a double-effect system), and are sent to the fractionating column C1. In the latter pratically all the $CO_2$ and $H_2O$ vapours are condensed as carbamate solution and sent to reactor R2.

Pure $NH_3$ ammonia at the head of the column C1 is condensed in E5 and the liquid ammonia obtained is used, together with the fresh $NH_3$ feed, as reflux for column C1 and feeds R2. The quantity of $NH_3$ reflux is determined by the thermal balance of column 1.

Consumptions

The specific consumptions, referring to 1000 kg of urea, are:

| | |
|---|---|
| Liquid NH3 at 32° C., 18 bar (kg) | 568 |
| CO2 (kg) | 734 |
| Steam at 25 bar (kg) | 600* |
| Electric power (kWh) | 130 |

*with the exception of water formation treatment.

EXAMPLE 2

Figure 2:
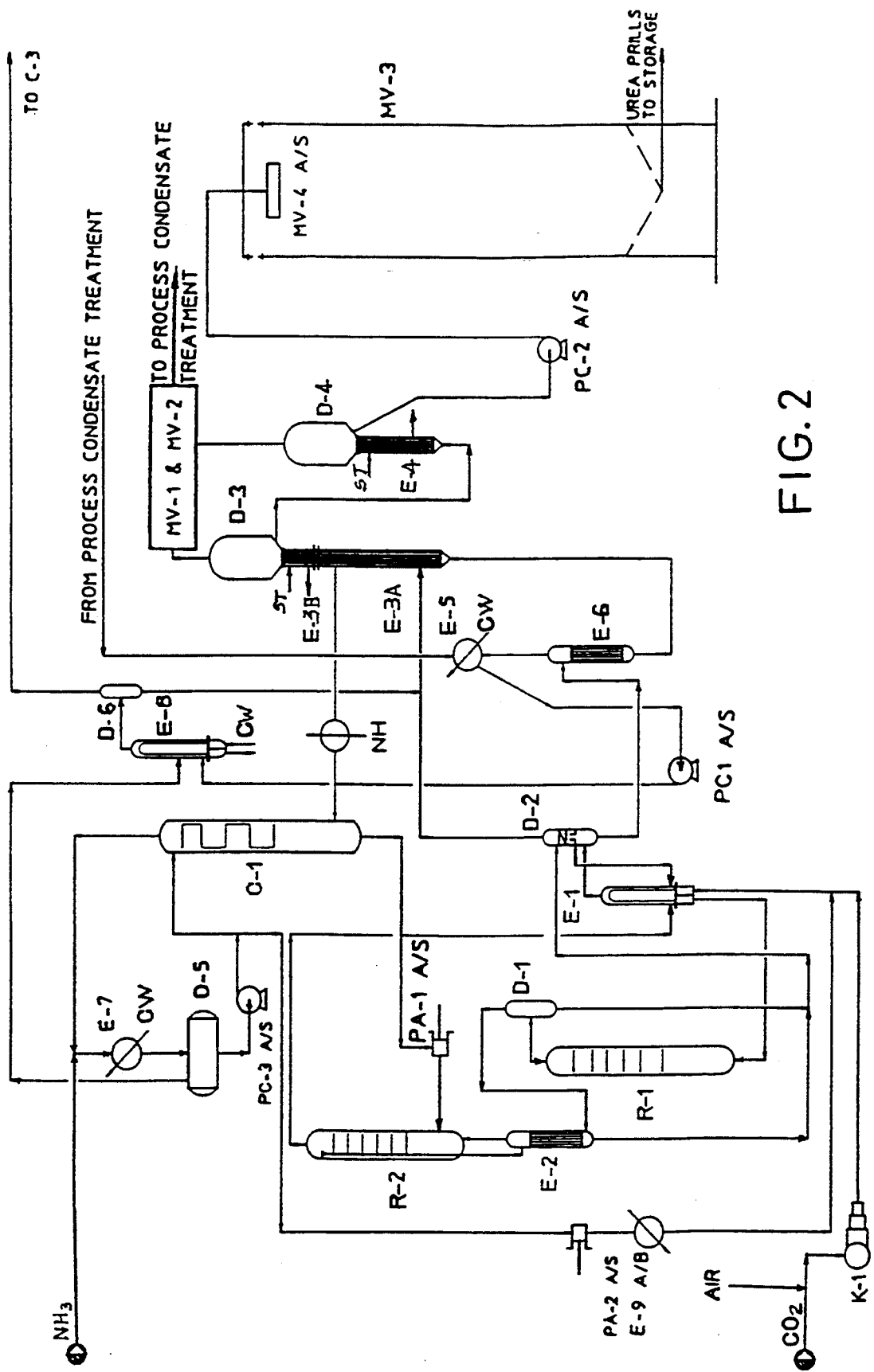

Heat Removal Process (FIG. 2)

The majority reaction A2) is carried out in the following conditions:

| | |
|---|---|
| NH3/CO2 mol | 3.5 ÷ 4 |
| H2O/CO2 mol | 0 |
| NH3 inlet temperature | ≈ 100° C. |
| CO2 inlet temperature | ≈ 150° C. |
| Reaction temperature | 195° C. |
| Pressure | 240 bar abs |
| Reactor conversion | 75% |
| Lining | AISI 316 L.U.G. |

The urea solution from reactor R1 undergoes flash from 240 to 150 bar in separator D1.

The vapours produced in flash in D1 (substantially ammonia) are sent to R2, while the urea solution in D1 is mixed with the solution from reactor D2 and feeds the medium pressure decomposer.

The operating conditions of the secondary reactor are:

| | |
|---|---|
| NH3/CO2 | 4.5 |
| H2O/CO2 | 1.3 |
| CO2 conversion yield | 60% |
| Pressure | 150 bar |
| Temperature | 190° C. |

75% of the urea production is obtained in R1, whereas the remaining 25% is obtained in R2.

The weighed average efficiency of the two reactors is close to 71.5%, that is very high in comparison to the efficiency of very recent processes.

Characteristically the $CO_2$ and fresh ammonia are fed by a medium pressure decomposer-prereactor E1 tube side, in which ammonium carbamate and urea are formed.

E1 is part of the majority reaction stage A2) with R1. A part of the reaction heat is removed from the urea solution that circulates outside said tubes.

Advantageously, this heat has a high thermal level (~170° C.) that is exploited for the distillation of the same urea solution ("process-to-process heat exchange").

The carbamate/urea solution in the pre-reactor E1 is sent to the reactor R1, in which the majority part of the carbamate is dehydrated to urea. Characteristically the control of the heat developed in E1 is carried out effecting the temperature of the liquid ammonia through E9, while the temperature of R1 is maintained by-passing, if necessary, the $CO_2$ to E1.

The auxiliary reactor R2 is fed with flash vapours and with the recycled carbamate solution, as well as with the vapours coming from the high pressures decomposer E2, preferably of falling-film type, the heat is given by means of medium pressure steam with the aim of performing the thermal balance of reactor R2 and to distill the solution coming from R2. The urea solution is then treated as in Example 1.

Consumptions

The specific consumptions, referring to 1000 kg of urea, are:

| | |
|---|---|
| Liquid $NH_3$ at 32° C., 18 bar (kg) | 568 |
| $CO_2$ (kg) | 734 |
| Steam at 25 bar (kg) | 400* |
| Electric power (kWh) | 115 |

*excluding water formation treatment.

EXAMPLE 3

Described hereunder, with a demonstrative aim, but not limitative, is the application of the invention to modernize existing Vulcan and Weatherly type plants.

These plants, developed in the U.S.A. in the years 1960–1970, are characterized by the fact that the synthesis reactor is fed with pure reagents ($NH_3$ and $CO_2$) without recycle water, which has enabled these plants to obtain very high conversion yields of $CO_2$ in urea (80% in the Vulcan reactor and 75% in the Weatherly reactor).

The operating data of these reactors are

| a) Vulcan reactor | |
|---|---|
| molar ratio $NH_3/CO_2$ | 4.5 |
| molar ratio $H20/CO_2$ | 0 |
| yield | 80% |
| pressure | 380 kg/cm2 abs |
| temperature | 215° C. |
| b) Weatherly Reactor | |
| $NH_3/CO_2$ molar ratio | 4 |
| $H_2O/CO_2$ molar ratio | 0 |
| yield | 75% |
| pressure | 260 kg/cm2 abs |
| temperature | 195° C. |

Figure 3:
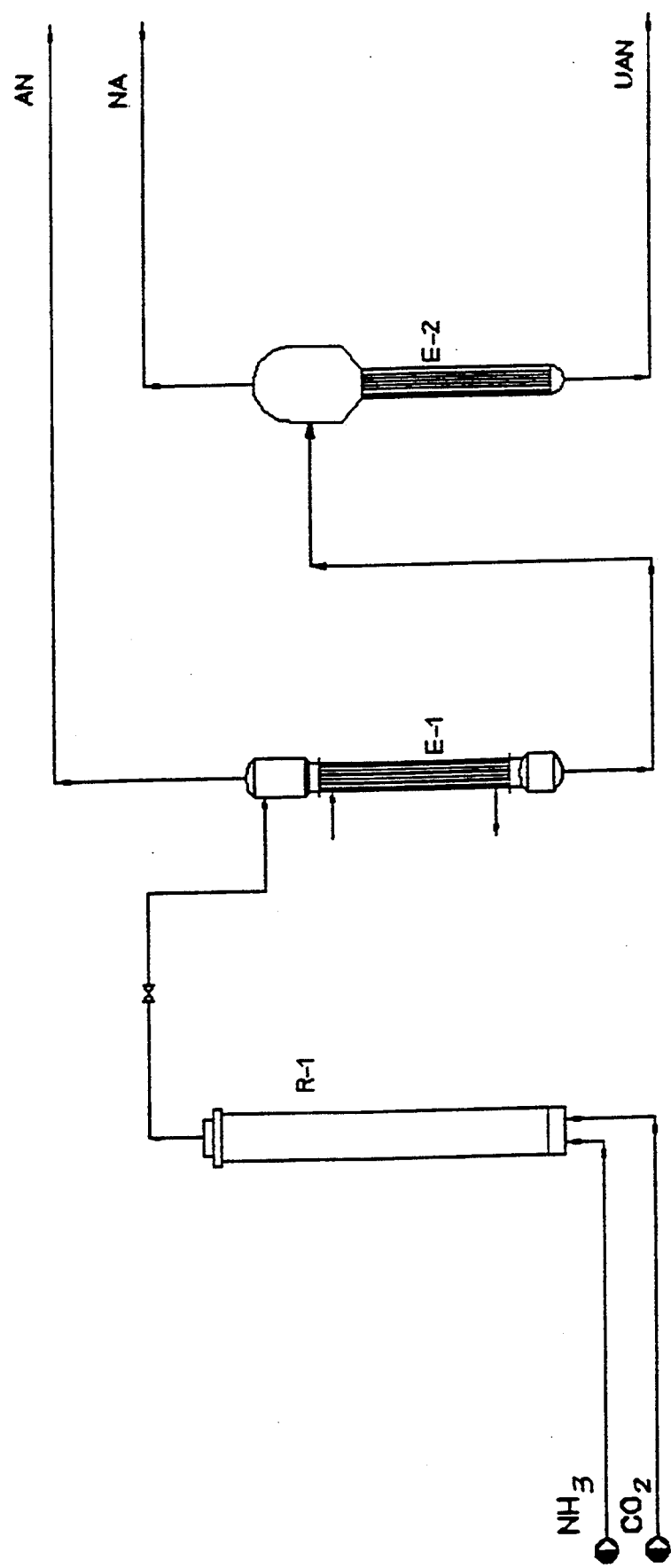
FIG. 3 is a flow diagram of a prior art process.

In FIG. 3 a process of Vulcan type is schematically shown, in its most simple version, in which the distillation vapours are used to produce nitric acid (AN line) and ammonium nitrate (NA line), while the urea solution is sent through the UAN line to the plant producing the aqueous urea and ammonium nitrate solution.

The urea solution at the reactor outlet (R-1) is distilled at medium (E-1) and low pressure (E-2) distillers (for instance 18 kg/cm2 abs and 2.5 kg/cm2 abs respectively) in such a way as to obtain a urea solution at 75÷80% urea weight to be utilized for the production of UAN (urea and ammonium nitrate aqueous solution). The distillation vapours, made up of mainly $NH_3$, are usually utilized as follows:

the vapours at 18 kg/cm2 abs for the production of nitric acid;
the vapours at 2.5 kg/cm2 for the production of ammonium nitrate.

In this way, all the $NH_3$ contained in the distillation vapours is recovered, while the $CO_2$ present is discharged into the atmosphere.

There exist even other variations to the utilization scheme for distillation products, variations aimed at the recovery of the $NH_3$ contained in vapours.

As another example, the vapours at 18 kg/cm2 abs can be sent to the fractionating column in order to produce $NH_3$ vapour at the head to be condensed and recycled in highly pure form to the synthesis reactor, and at the tail carbamate solution to be decomposed at low pressure for the use of $NH_3$ in the production of ammonium nitrate.

In some cases these vapours are purified from the $CO_2$ by washing them with an alkaline solution (for instance MEA), and then condensed and recycled to the reactor, while the exhausted MEA solution is distilled in order to separate the $CO_2$ that can be either discharged into the atmosphere and/or recycled. It should be noted that the latter operation is very expensive in terms of energy consumption and plant cost.

The aim of this invention is to provide a method that permits a simple, inexpensive, efficient and convenient extension of Swiss application no. 03216/90-1 to the existing urea synthesis plant of the "once through" type, mainly Vulcan and Weatherly processes. Particularly, the Vulcan synthesis section and the Weatherly synthesis section of these plants represents the majority portions A1 and A2 respectively, described in the mentioned claims.

The main characteristics of the method, according to the invention, are described in the aforementioned claims.

In fact, it has been found that it is surprisingly possible to revamp, in a simple and safe manner, using this invention's processes as described and claimed, existing urea production plants of the "once through" type, according to the modalities herein described.

These "once through" plants present the following main disadvantages:

partial utilization of the $CO_2$ fed to the reactor, connected to the yield of the reactor itself (in the Vulcan reactor, with a yield equal to 80%, only 80% of the fed $CO_2$ is converted into urea, while in the Weatherly process this yield is 75%), whereas in total recycle plants the utilization $CO_2$ yield is equal to approximately 100%;

very high energy consumptions in the case of residual $CO_2$ recovery through the use of an absorbing solution as the MEA type;

very little operating flexibility, the urea plant's run being bound to the utilization of gaseous effluents (vapours rich in $NH_3$) in other plants.

The capacity of the plant in the example is equal to 1000 MTD urea, as aqueous solution at 77% urea weight, and large quantities of $NH_3$ contained in the distillation vapours are recovered in different plants (for example 9770 kg/h $NH_3$ in the vapour stream at 18 kg/cm2 abs and 8970 kg/h of $NH_3$ in the stream at 2.5 kg/cm2 abs.

The $CO_2$ fed to the plant is 38193 kg/h, of which 30554 kg/h is transformed into urea.

Figure 4:
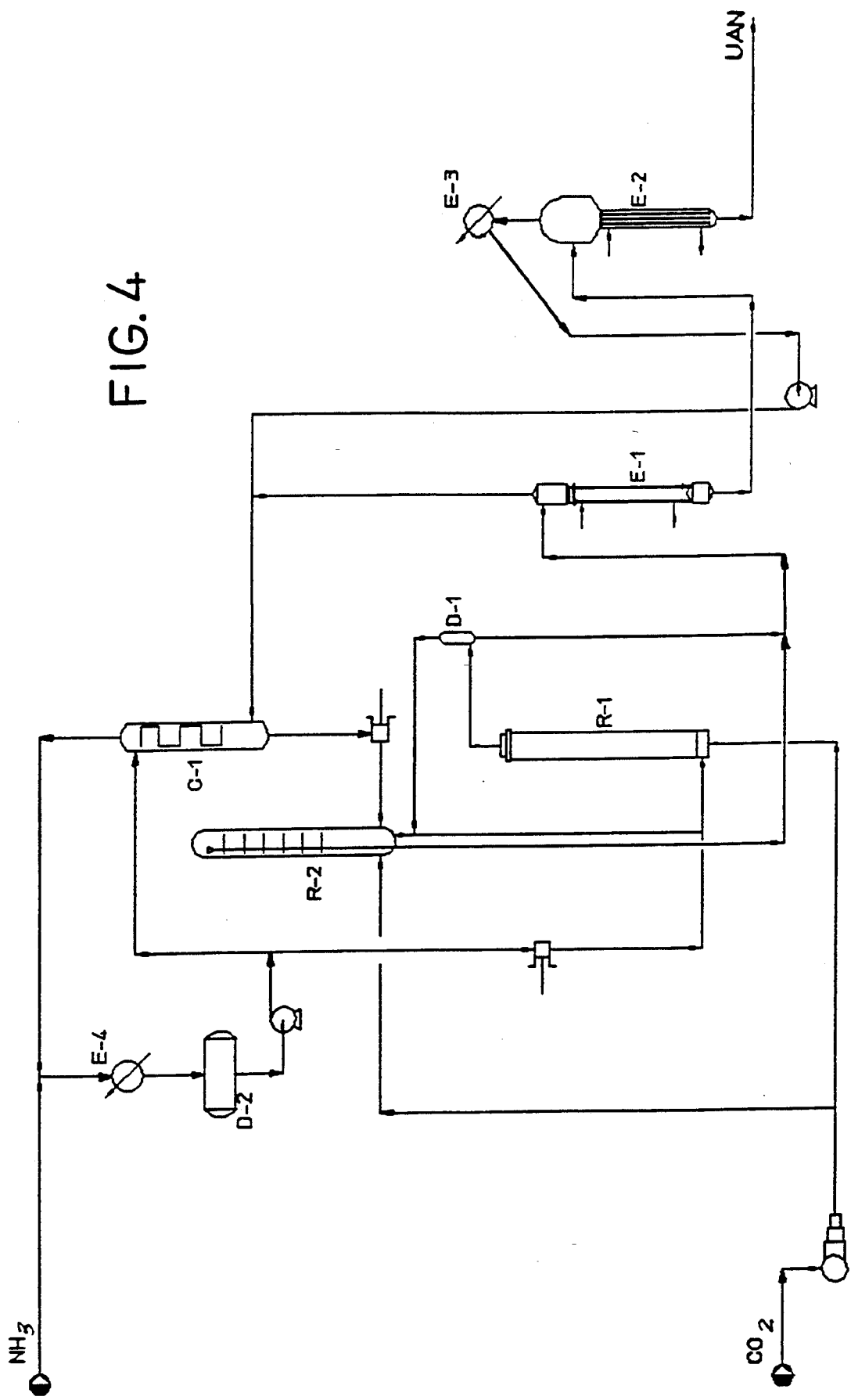
FIG. 4 is a flow diagram of that process modified in accordance with the present invention.

In FIG. 4 the same plant is shown, revamped according to the urea differentiated yield process, object of this invention.

The vapours exiting from the existing low pressure distiller E-2 are condensed in E-3 (*) and sent to the fractionating column C-1 (*), together with the medium pressure vapours coming from the existing decomposer E-1. For this column can (*) new equipment be obtained, at the head, highly pure ammonia vapour that, after condensing in E-4(*), is recycled to the high yield reactor R-1 (existing), while at the bottom a carbamate solution is obtained that feeds the auxiliary reactor.

The reactor R-2(*), that has a conversion yield equal to 60–62%, is fed even with flash vapours (rich in ammonia), that are released in the separator D-1 (*) and with $CO_2$ in quantities that enable the reactor's thermal balance to be performed.

The production of urea, consequent to the total recovery of the CO$_2$ feed, results being equal to 1250 MTD, i.e. 25% more in comparison to the quantity produced in "once through" type reactors. Moreover, the vapour streams directed towards the outside are eliminated.

An optimum production distribution between the two reactors is equal to 70% for the Vulcan type reactor and 30% for the auxiliary reactor, and the average conversion yield of the two reactors equals 70%, a higher value than the one that can be obtained in conventional plants.

In the aforementioned example it was foreseen to produce urea in an aqueous solution to be sent to another plant for the production of UAN.

By adding a conventional vacuum concentration section (not indicated on the FIG. 4), it is possible to obtain a total recycle plant.

Among the main advantages of the process according to the invention, the following are mentioned:

1) High urea yield in the synthesis section with consequent recycle sections downstream simple and inexpensive.
2) Elimination of all critical equipment subject to corrosion, used in modern stripping processes, such as strippers, high pressure carbamate condensers, scrubbers, etc., resulting in a longer life of the plant.
3) Very low carbamate recycle to the low pressure converter (with respect to conventional high pressure total recycle processes) and very small carbamate pumps.
4) Very low utility and energy consumptions.
5) Absence of recovery steam generation in the plant with consequently minor heat transfer surface requirements, and absence of recovery steam to be used elsewhere.
6) Reduced investment costs.

We claim:

1. A process of producing urea in a plant including at least one reaction space for reacting ammonia and carbon dioxide at high temperature and pressure and a recovery section for recovering unreacted reagents, comprising the steps of:
   (a) reacting highly pure ammonia and carbon dioxide with partial removal of the reaction heat in a first reaction stage at a predetermined pressure less than 300 kg/cm$_2$ abs, at a temperature not higher than about 200° C. and at an ammonia/carbon dioxide ratio less than 4;
   (b) flash separating a product stream from the first reaction stage at a pressure at least 30% lower than the pressure in the first reaction stage into a gaseous effluent and a liquid effluent;
   (c) reacting the gaseous effluent thus obtained and a carbamate solution recycled from the recovery section in a second reaction stage at a pressure less than 200 kg/cm$_2$ abs and at a temperature sufficient to carry out the reaction, the predetermined pressure in the first reaction stage being greater than the pressure in the second reaction stage;
   (d) feeding the liquid effluents from said first and second reaction stages to the recovery section, decomposing the liquid effluents in the recovery section, withdrawing a urea solution and a carbamate solution therefrom, and recycling the carbamate solution to said second reaction stage.

2. A process according to claim 1, wherein the first reaction stage operates at a pressure of about 240 kg/cm$^2$ abs.

3. A process according to claim 1, wherein said flash separation is carried out at a pressure of about 150 kg/cm$^2$ abs.

4. A process according to claim 1, wherein about 75% of the urea is produced in the first reaction stage and about 25% of the urea is produced in the second reaction stage.

5. A process according to claim 1, wherein the reaction between highly pure ammonia and carbon dioxide in said first reaction stage is carried out in a decomposer-prereactor and in a synthesis reactor in series, the reaction heat being partially removed in said decomposer-prereactor.

6. A process according to claim 2, wherein the liquid effluents from said first and second reaction stages are decomposed in at least one decomposition stage by means of the reaction heat removed in said decomposer-prereactor.

7. A process according to claim 1, further comprising the step of recycling to the first reaction stage an ammonia stream obtained by decomposing in the recovery section the liquid effluents from said first and second reaction stages.

8. A process according to claim 5, wherein the removal of the reaction heat in the first reaction stage is controlled by regulating the temperature of the ammonia stream recycled from the recovery section.

9. A process according to claim 7, wherein the removal of the reaction heat in the first reaction stage is controlled by regulating the temperature of the ammonia stream recycled from the recovery section.

10. A process according to claim 5, wherein the removal of the reaction heat in the first reaction stage is controlled by directly feeding part of the carbon dioxide to said synthesis reactor.

11. A process according to claim 1, further comprising the step of distilling the liquid effluent from the second reaction stage in a high pressure decomposer.

12. A process according to claim 11, wherein said distillation step is carried out by countercurrently contacting in the high pressure decomposer the liquid effluent from the second reaction stage and the gaseous effluent from the first reaction stage.

* * * * *